(12) United States Patent
Hefti et al.

(10) Patent No.: US 8,557,222 B2
(45) Date of Patent: Oct. 15, 2013

(54) RADIOPHARMACEUTICAL IMAGING OF NEURODEGENERATIVE DISEASES

(75) Inventors: Franz F. Hefti, Bernardsville, NJ (US); Daniel M. Skovronsky, Glen Mills, PA (US); Alan P. Carpenter, Jr., Carlisle, MA (US)

(73) Assignee: Avid Radiopharmaceuticals, Inc., Philadelphia, PA (US)

( * ) Notice: Subject to any disclaimer, the term of this patent is extended or adjusted under 35 U.S.C. 154(b) by 819 days.

(21) Appl. No.: 12/418,177

(22) Filed: Apr. 3, 2009

(65) Prior Publication Data

US 2009/0257949 A1    Oct. 15, 2009

Related U.S. Application Data

(60) Provisional application No. 61/042,480, filed on Apr. 4, 2008.

(51) Int. Cl.
*A61M 36/04* (2006.01)

(52) U.S. Cl.
USPC .......................... 424/1.61; 424/1.89; 424/1.73

(58) Field of Classification Search
None
See application file for complete search history.

(56) References Cited

U.S. PATENT DOCUMENTS

| | | | |
|---|---|---|---|
| 3,904,530 | A | 9/1975 | Martone et al. |
| 6,696,039 | B2 | 2/2004 | Kung et al. |
| 6,770,259 | B2 | 8/2004 | Carpenter, Jr. |
| 6,946,116 | B2 | 9/2005 | Kung et al. |
| 7,250,525 | B2 | 7/2007 | Kung et al. |
| 2003/0013950 | A1 | 1/2003 | Rollo et al. |
| 2003/0236391 | A1 | 12/2003 | Klunk et al. |
| 2005/0043523 | A1 | 2/2005 | Klunk et al. |
| 2005/0271584 | A1 | 12/2005 | Kung et al. |
| 2006/0269473 | A1 | 11/2006 | Kung et al. |
| 2006/0269474 | A1 | 11/2006 | Kung et al. |
| 2007/0031328 | A1 | 2/2007 | Kung |
| 2007/0281299 | A1 | 12/2007 | Youdim et al. |
| 2008/0038195 | A1 | 2/2008 | Kung et al. |

FOREIGN PATENT DOCUMENTS

| | | |
|---|---|---|
| EP | 181572 A2 | 5/1986 |
| EP | 1655287 A1 | 5/2006 |
| WO | WO92/18881 A1 | 10/1992 |
| WO | WO2005/016888 A1 | 2/2005 |
| WO | WO2006/014381 A2 | 2/2006 |
| WO | WO2006/057323 A1 | 6/2006 |
| WO | WO2006/066104 A2 | 6/2006 |
| WO | WO2006/078384 A2 | 7/2006 |
| WO | WO2007/047204 A1 | 4/2007 |
| WO | WO2007/086800 A1 | 8/2007 |
| WO | WO2007/126733 A2 | 11/2007 |
| WO | WO2009/124273 A2 | 10/2009 |

OTHER PUBLICATIONS

Kudo et al. 2-(2-[2-Dimethylaminothiazol-5-yl]ethenyl)-6-(2-[fluoro]ethoxy)benzoxazole: a novel PET agent for in vivo detection of dense amyloid plaques in Alzheimer's disease patients. J Nucl Med. Apr. 2007;48(4):553-61.*

(Continued)

*Primary Examiner* — Gregory S Emch
(74) *Attorney, Agent, or Firm* — Pepper Hamilton LLP

(57) ABSTRACT

Methods for simultaneously detecting dementia or cognitive impairment, such as Alzheimer's Disease (AD), Parkinson's Disease (PD), Lewy Body Dementia (LBD) and Vascular Dementia (VaD) in a patient using dual or multiple radiopharmaceutical probes are provided herein.

12 Claims, 12 Drawing Sheets

(56) References Cited

OTHER PUBLICATIONS

Hilker et al. Positron emission tomographic analysis of the nigrostriatal dopaminergic system in familial parkinsonism associated with mutations in the parkin gene. Ann Neurol. Mar. 2001;49(3):367-76.*
Ma et al. Dual SPECT of dopamine system using [99mTc]TRODAT-1 and [123I]IBZM in normal and 6-OHDA-lesioned formosan rock monkeys.Nucl Med Biol. Jul. 2002;29(5):561-7.*
O'Brien. Role of imaging techniques in the diagnosis of dementia. British Journal of Radiology (2007) 80, S71-S77.*
Souza, et al., Longitudinal noninvasive PET-based β cell mass estimates in a spontaneous diabetes rat model, *The Journal of Clinical Investigation* (Jun. 2006), 116(6):1506-1513.
Zhang, et al., F-18 Stilbenes as PET Imaging Agents for Detecting β-Amyloid Plaques in the Brain, *J. Med. Chem.* (Aug. 23, 2005), 48(19):5980-5988.
Ashburn, et al., Amyloid probes based on Congo Red distinguish between fibrils comprising different peptides, *Chemistry & Biology* (May 1996), 3(5):351-358.
Han, et al., Technetium Complexes for the Quantitation of Brain Amyloid, *J. Am. Chem. Soc.* (May 8, 1996), 118(18):4506-4507.
Klunk, et al., Quantitative in vitro NMR analysis of Alzheimer's, non-Alzheimer's demented and Control Brain, *Biol. Psychiatry* (May 1, 1994), 35(9):627.
Klunk, et al., Chrysamine-G Binding to Alzheimer and Control Brain: Autopsy Study of New Amyloid Probe, *Neurobiol. Aging* (1995), 16(4):541-548.
Klunk, et al., Staining of AD and Tg2576 Mouse Brain with X-34, a Highly Fluorescent Derivative of Chrysamine G and a Potential in Vivo Probe for β-sheet Fibrils, *Soc. Neurosci. Abstr.* (1997), 23:1638, Abstract No. 636.12.
Mathis, et al., Synthesis of a Lipophilic, Radioiodinated Ligand with High Affinity to Amyloid Protein in Alzheimer's Disease Brain Tissue, *J. Labelled Cpd. Radiopharm* (1997) 40:94-95.
Lorenzo, et al., β-Amyloid neurotoxicity requires fibril formation and is inhibited by Congo red, *Proc. Natl. Acad. Sci. U.S.A.* (Dec. 1994), 91:12243-12247.
Zhen, et al., Synthesis and Amyloid Binding Properties of Rhenium Complexes: Preliminary Progress Toward a Reagent for SPECT Imaging of Alzheimer's Disease Brain, *J. Med. Chem.* (Jul. 2, 1999), 42(15):2805-2815.
Zhang, et al., $^{18}$F-labeled Styrylpyridines as PET agents for Amyloid Plaque Imaging, *Nuclear Medicine and Biology* (2007), 34:89-97.
Henriksen, et al., Development and Evaluation of Compounds for Imaging of β-amyloid Plaque by Means of Positron Emission Tomography, *Eur J Nucl Med Mol Imaging* (Jan. 26, 2008), 35(1):S75-S81.
Lemaire et al., Solid Phase Extraction—An Alternative to the Use of Rotary Evaporators for Solvent Removal in the Rapid Formulation of PET Radiopharmaceuticals, *J Labelled Cpd. Radiopharm.* (1999), 42:63-75.
Tofe, et al., In Vitro Stabilization of a Low-Tin Bone-Imaging Agent ($^{99m}$TC-Sn-HEDP) by Ascorbic Acid, *J Nucl Med*, (1976), 17(9):820-825.
Knapp, et al., Availability of Rhenium-188 from the Alumina-Based W-188/ Rhenium-188 Generator for Preparation of Rhenium-188-Labelled Radiopharmaceuticals for Cancer Treatment, *Anticancer Research* (1997), 17:1783-1796.
Liu, et al., Ascorbic Acid: Useful as a Buffer Agent and Radiolytic Stabilizer for Metalloradiopharmaceuticals, *Bioconjugate Chemistry* (Aug. 19, 2003), 14(5):1052-1056.
Firnau, et al., Aromatic Radiofluorination with [$^{18}$F]Flurine Gas: 6-[$^{18}$F]Fluoro-L-Dopa, *J Nucl Med* (1984), 25(11):1228-1233.
Choi, et al., Preclinical Properties of $^{18}$F-AV-45: A PET Agent for Aβ Plaques in the Brain, *J Nucl Med*, (Oct. 16, 2009) 50(11):1887-1894.
Glowienke, et al., Structure-activity considerations and in vitro approaches to assess the genotoxicity of 19 methane-, benzene- and toluenesulfonic acid esters, *Mutat Res.*, (Dec. 21, 2004), 581(1-2):23-34.
Schyler, PET Tracers and Radiochemistry, *Ann Acad Med Singapore*, (Mar. 2004); 33(2): 146-154.
Bates et al., Clearance Mechanisms of Alzheimer's Amyloid-β Peptide: Implications for Therapeutic Design and Diagnostic Tests, *Molecular Psychiatry* (Sep. 16, 2008), 1-18.
Bauer et al., A Positron Emission Tomography Microdosing Study With a Potential Antiamyloid Drug in Healthy Volunteers and Patients With Alzheimer's Disease, *Clin. Pharmacol. Ther.* (Sep. 2006), 80(3):216-227.
Zhang et al., $^{18}$F-Labeled Styrylpyridines as PET Agents for Amyloid Plaque Imaging, *Nuclear Medicine and Biology* (2007), 34:89-97.
Mathis et al., Synthesis and Evaluation of $^{11}$C-Labeled 6-Substituted 2-Arylbenzothiazoles as Amyloid Imaging Agents, *J. Med. Chem.* (May 24, 2003), 46(13):2740-2754.
Small et al., PET of Brain Amyloid and Tau in Mild Cognitive Impairment, *New Engl. J. Med.* (Dec. 21, 2006), 355(25):2652-2663.
Zhang et al., F-18 Polyethyleneglycol Stilbenes as PET Imaging Agents Targeting Aβ Aggregates in the Brain, *Nucl. Med. Biol.* (Jun. 2, 2005), 32:799-809.
Ono et al., Benzofuran Derivatives as Aβ-Aggregate-Specific Imaging Agents for Alzheimer's Disease, *Nucl. Med. Biol.* (Aug. 2002), 29(6):633-642.
Ono et al., Synthesis and Biological Evaluation of (E)-3-Styrylpyridine Derivatives as Amyloid Imaging Agents for Alzheimer's Disease, *Nucl. Med. Biol.* (May 2005), 32(4):329-335.
Qu et al., Radioiodinated Aza-Diphenylacetylenes as Potential SPECT Imaging Agents for β-Amyloid Plaque Detection, *Bioorg. Med. Chem. Lett.* (Apr. 25, 2007), 17:3581-3584.
Kemppainen et al., PET Amyloid Ligand [$^{11}$C]PIB Uptake is Increased in Mild Cognitive Impairment, *Neurology* (May 8, 2007), 68:1603-1606.
Pike et al., β-Amyloid Imaging and Memory in Non-Demented Individuals: Evidence for Preclinical Alzheimer's Disease, *Brain* (Oct. 10, 2007), 130(11):2837-2844.
Klunk et al., Imaging Brain Amyloid in Alzheimer's Disease with Pittsburgh Compound-B, *Ann. Neurol.* (Jan. 21, 2004), 55(3):306-319.
Verhoeff et al., In-Vivo Imaging of Alzheimer Disease β-Amyloid with [$^{11}$C]SB-13 PET, *Am. J. Geriatr. Psychiatry* (Nov.-Dec. 2004), 12(6):584-595.
Newberg et al., Safety, Biodistribution, and Dosimetry of $^{123}$I-IMPY: A Novel Amyloid Plaque-Imaging Agent for the Diagnosis for Alzheimer's Disease, *J. Nucl. Med.* (May 2006), 47(5):748-754.
Kung et al., Radiopharmaceuticals for Single-Photon Emission Computed Tomography Brain Imaging, *Semin. Nucl. Med.* (Jan. 2003), 33(1):2-13.
Kung et al., Characterization of Optically Resolved 9-Fluoropropyl-Dihydrotetrabenazine as a Potential PET Imaging Agent Targeting Vesicular Monoamine Transporters, *Nucl. Med. Biol.* (2007), 34:239-246.
Kilbourn et al., Pharmacokinetics of [$^{18}$F]Fluoroalkyl Derivatives of Dihydrotetrabenazine in Rat and Monkey Brain, *Nucl. Med. Biol.* (2007), 34(3):233-237.
Sandler et al., Evaluation of Myocardial Ischemia Using a Rest Metabolism/Stress Perfusion Protocol with Fluorine-18 Deoxyglucose/Technetium-99m MIBI and Dual-Isotope Simultaneous-Acquisition Single-Photon Emission Computed Tomography, *Journal of the American College Cardiology* (Oct. 1995), 26(4):870-878.
Rockwood, Mixed Dimentia: Alzheimer's and Cerebrovascular Disease, *International Psychogeriatrics* (2003), 15 (Suppl. 1):39-46.
Langa et al., Mixed Dimentia: Emerging Concepts and Therapeutic Implications, *JAMA* (Dec. 15, 2004), 292(23):2901-2908.
Jellinger, Morphological Substrates of Parkinsonism With and Without Dementia: A Retrospective Clinico-Pathological Study, J. Neural. Transm. (2007), (Suppl. 72):91-104.
www.alz.org/alzheimers_disease_mixed_dementia.asp Mixed Dementia, Jul. 30, 2009, Printed Sep. 17, 2009.

(56) References Cited

OTHER PUBLICATIONS

Ito et al., PET and Planar Imaging of Tumor Hypoxia With Labeled Metronidazole, Acad. Radiol. (May 2006), 13(5):598-609.
Bisdas et al., Dynamic Contrast-Enhanced CT of Head and Neck Tumors: Comparison of First-Pass and Permeability Perfusion Measurements Using Two Difference Commercially Available Tracer Kinetics Models, Acad. Radiol. (Dec. 2008), 15(12):1580-1589.
Matsuda, Role of Neuroimaging in Alzheimer's Disease, With Emphasis on Brain Perfusion SPECT, J. Nucl. Med. (Aug. 2007), 48(8):1289-1300.
Yang et al., Greater Availability of Dopamine Transporters in Patients With Major Depression—A Dual-Isotope Spect Study, Psychiatry Research: Neuroimaging (Apr. 15, 2008), 162(3):230-235.
Djaldetti et al., [123I]-FP-CIT SPECT and Olfaction Test in Patients With Combined Postural and Rest Tremor, J. Neural. Transm. (Feb. 4, 2008), 115(3):469-472.
Stoffers et al., Early-Stage [123I]β-CIT SPECT and Long-Term Clinical Follow-Up in Patients With an Initial Diagnosis of Parkinson's Disease, Eur. J. Nucl. Med. Mol. Imaging (Jan. 29, 2005), 32(6):689-695.
Harris et al., VMAT2 Gene Expression and Function as it Applies to Imaging β-Cell Mass, *J. Mol. Med*. (Jul. 31, 2007), 86(1):5-16.

\* cited by examiner

RADIOPHARMACEUTICAL IMAGING OF NEURODEGENERATIVE DISEASES

CROSS-REFERENCE TO RELATED APPLICATIONS

This application claims priority under 35 U.S.C. §119(e) to U.S. Provisional Patent Application Ser. No. 61/042,480, filed Apr. 4, 2008, the disclosure of which is incorporated by reference in its entirety.

TECHNICAL FIELD

The invention presented herein relates generally to monitoring neurodegenerative diseases in the human brain by means of radiopharmaceutical imaging by positron emission tomography or single photon emission computed tomography. More specifically, the present invention relates to the differential detection of neurodegenerative processes in the brains of patients with cognitive impairment or movement disorders using two or more different brain imaging radiopharmaceuticals.

BACKGROUND

Alzheimer's Disease (AD) is a progressive neurodegenerative disorder characterized by cognitive decline, irreversible memory loss, disorientation and language impairment. It is the most common cause of dementia in the United States. AD can strike persons as young as 40-50 years of age, but because the presence of the disease is difficult to detect without histopathological examination of brain tissue, the time of onset in living subjects is unknown. The prevalence of AD increases with age, with estimates of the affected population as high as 40% by ages 85-90.

AD is only definitively diagnosed through postmortem examination of brain tissue, when pathologists examine the brain tissue for the presence of abundant senile plaques (SPs) composed of amyloid-β (Aβ) peptide aggregates and neurofibrillary tangles (NFTs) formed by filaments of highly phosphorylated tau proteins. An amyloid deposit is formed by the aggregation of amyloid peptides, followed by the further combination of aggregates and/or amyloid peptides. The fibrillar aggregates of amyloid peptides, Aβ1-40 and Aβ1-42, are major metabolic peptides derived from amyloid precursor protein that are found in senile plaques and cerebrovascular amyloid deposits in AD patients.

Parkinson's Disease (PD), another common neurodegenerative disease, is a progressive disorder characterized by resting tremors, bradykinesia, muscular rigidity, and postural instability. PD affects men and women without distinction, regardless of social, ethnic, economic or geographic backgrounds. PD usually develops after the age of 60, though 15% of those diagnosed are under the age of 50. Family history of PD is an etiological factor for 5-10% of patients diagnosed with the disease, yet only 1% of cases have been shown to be clearly familial. It is estimated that 1.5 million Americans are currently living with Parkinson's Disease.

Dementia with Lewy Bodies (DLB) is a progressive neurodegenerative disorder characterized by symptoms that fluctuate between various degrees of manifestation. Such symptoms include progressive dementia, Parkinsonian movement difficulties, hallucinations, and increased sensitivity to neuroleptic drugs. As with AD, advanced age is considered to be a risk factor for DLB, with average onset typically between the ages of 50-85. 20% of all dementia cases are caused by DLB and over 50% of PD patients develop Parkinson's Disease Dementia (PDD), a type of DLB. DLB may occur alone or in conjunction with other brain abnormalities, including those involved in AD and PD, as mentioned above. Currently, conclusive diagnosis of DLB is made during postmortem autopsy.

PD and DLB share an etiology of dopamine deficiency, which is correlated with the death of dopaminergic neurons in the substantia nigra. Dopamine is a neurotransmitter that allows for smooth, coordinated function of the body's muscles and movement. The cause of dopaminergic neuronal death in PD is unknown, but it is recognized that in DLB, abnormal protein deposits called Lewy body proteins or "Lewy bodies" are instrumental in the death of dopaminergic neurons. Lewy bodies occur mostly in the substantia nigra and locus ceruleus sections of the brain stem and also, to a lesser extent, in the subcortical and cortical regions of the brain. Because of this specific localization in the brain, Lewy bodies also interfere with the production of acetylcholine, causing disruption in perception, thinking and behavior. Lewy bodies are also typically considered to be a type of SP, as Lewy bodies are made up of aggregated α-synuclein protein deposits.

An additional etiology of neurodegeneration can be a mixture of pathologies that involves a component of microvascular, or perfusion, deficits in the brain. Commonly referred to as "mixed dementia", this type of neurodegeneration often involves both perfusion deficits as well as amyloid plaque pathology. Different meanings have been associated with the term mixed dementia. One definition of mixed dementia encompasses a combination of AD and other pathologies such as hypothyroidism, or vitamin B-12 deficiency. However, mixed dementia is most commonly refers to the coexistence of AD and vascular dementia (VaD). Mixed dementia is clinically important because the combination of AD and VaD may have a greater impact on the brain than either by itself. Mixed dementia is traditionally difficult to diagnose, although symptoms are generally similar to those of AD or VaD or a combination of the two.

Because of the central role of the presence of Aβ plaques in AD and death of dopaminergic neurons in PD and DLB, there has been a wide interest in developing radiolabeled ligands that bind to and allow imaging of such abnormalities. Several radioisotopically-labeled Aβ-aggregate-specific ligands have been reported for the imaging of amyloid plaque in the living subject using positron emission tomography (PET) or single photon emission computed tomography (SPECT). These ligands are mainly targeted to nigrostriatal neurons and D2/D3 receptors in the brain. Examples of such radioisotopically-labeled Aβ-aggregate-specific ligands include [(99m)Tc]TRODAT-1 and [(123)I]IBZM, among many others. In addition, several radiopharmaceuticals have been used for PET or SPECT imaging of regional cerebral perfusion. PET radiopharmaceuticals such as $^{15}$O-labeled water ($H_2$$^{15}$O) and $^{13}$N-ammonia ($^{13}$NH$_3$) have been employed for perfusion imaging. SPECT radiopharmaceuticals such as Tc-99m HMPAO and Tc-99m Bicisate are also used as cerebral perfusion agents.

Dual-isotope imaging techniques have been employed in trials including parathyroid-studies to detect the existence of an adenoma on the thyroid and in myocardial imaging studies of perfusion and myocardial tissue viability. Additionally, in the brain, a simultaneous $^{18}$F-FDG and $^{99m}$Tc-HMPAO SPECT imaging technique has been utilized to image selected areas in the neuroanatomy of anxiety and depression such as the hippocampus, basal ganglia and gyri temporales superiores. There have also been studies employing a dual SPECT imaging technique with [$^{99m}$Tc]TRODAT-1 and [$^{123}$I]IBZM to image nigrostriatal neurons and D2/D3 receptors.

SUMMARY

Embodiments of the present invention provide a method for differentially detecting multiple pathologies or diseased states of the brain, including administering a first radiopharmaceutical for detecting a structure associated with a first diseased state to a patient, administering a second radiopharmaceutical for detecting a structure associated with a second diseased state to the patient, imaging a portion of a brain of the patient comprising a region of the brain wherein the structures associated with the first diseased state and the second diseased state are expected to be positioned, and detecting the first diseased state, the second diseased state or both the first diseased state and the second diseased state in sequential or simultaneous nuclear imaging procedures. In some embodiments, the steps of administering the first radiopharmaceutical and administering the second radiopharmaceutical are performed concurrently.

In some aspects of the present invention, the first diseased state includes at least one of dementia, cognitive impairment, Alzheimer's Disease (AD), Parkinson's Disease (PD), Dementia with Lewy Bodies (DLB), Vascular Dementia (VaD), and combinations thereof. In other aspects, the second diseased state includes at least one of dementia, cognitive impairment, Alzheimer's Disease (AD), Parkinson's Disease (PD), Dementia with Lewy Bodies (DLB), Vascular Dementia (VaD), and combinations thereof.

In certain embodiments, the step of imaging includes positron emission tomography (PET) imaging, single photon emission computed tomography (SPECT) imaging, PET with concurrent computed tomography imaging (PET/CT), PET with concurrent magnetic resonance imaging (PET/MRI), SPECT with concurrent CT imaging (SPECT/CT), or a combination thereof.

The method for detecting multiple diseased states of certain embodiments further includes the step of waiting for a period of time following administration of the first radiopharmaceutical. In other embodiments, the method for detecting multiple diseased states includes waiting for a period of time following administration of the second radiopharmaceutical. In yet other embodiments, the method further includes the step of administering a third radiopharmaceutical.

Other embodiments of the present invention are directed to a method for detecting multiple diseased states or pathologic processes in a patient including administering an effective amount of a radiopharmaceutical targeted to β-amyloid plaque to a patient, wherein the β-amyloid plaque is associated with a first diseased state or pathologic process, acquiring an image to detect the presence or absence of the β-amyloid plaque in the cortical regions of the brain of the patient, administering an effective amount of a metabolic imaging radiopharmaceutical, wherein the metabolic imaging radiopharmaceutical corresponds to glucose utilization in the brain of the patient and wherein a decrease in the metabolic imaging radiopharmaceutical signal is associated with a second diseased state or pathologic process, acquiring an image to detect metabolic activity of the brain of the patient, detecting the presence or absence of the first diseased state or pathologic process, and detecting the presence or absence of the second diseased state or pathologic process. The metabolic imaging radiopharmaceutical of certain embodiments comprises [$^{18}$F]fluorodeoxyglucose $^{18}$FDG. The radiopharmaceutical targeted to β-amyloid plaque of certain embodiments comprises ((E)-4-(2-(6-(2-(2-(2-[$^{18}$F]fluoroethoxy)ethoxy)ethoxy)pyridin-3-yl)vinyl)-N-methylbenzenamine)) $^{18}$F-AV-45. In some aspects of the invention, the effective amount of $^{18}$F-AV-45 includes from about 0.1 to about 20 mCi. In certain aspects, the effective amount of $^{18}$F-AV-45 includes about 10 mCi. In additional aspects of the invention, an effective amount of $^{18}$FDG, between 0.1 to about 20 mCi, may be administered to a human subject followed by imaging either prior to, concurrently with, or following the administration and another PET brain imaging radiopharmaceutical, such as AV-45 for imaging the β-amyloid plaques or AV-133 for imaging VMAT2 as a marker of dopaminergic neuronal integrity.

In some embodiments, the step of administering the radiopharmaceutical targeted to β-amyloid plaque and the step of administering the metabolic imaging radiopharmaceutical are performed concurrently. In other embodiments, the step of acquiring an image to detect the presence or absence of the β-amyloid plaque in the cortical regions of the brain of the patient and the step of acquiring an image to detect metabolic activity of the brain of the patient are performed concurrently. In some embodiments, the method for detecting multiple diseased states in a patient further includes normalizing the image intensity of the acquired images to a reference region, such as the cerebellum of the brain of the patient. In certain embodiments, the steps of detecting the first diseased state or pathologic process and detecting the second diseased state or pathologic process are performed sequentially. In other embodiments, these steps are performed concurrently.

Other embodiments of the present invention are directed to a method for detecting multiple diseased states or pathologic processes in a patient including administering an effective amount of a radiopharmaceutical targeted to β-amyloid plaque to a patient, wherein the β-amyloid plaque is associated with a first diseased state or pathologic process, acquiring an image to detect the presence or absence of the β-amyloid plaque in the cortical regions of the brain of the patient, administering an effective amount of a radiopharmaceutical targeted to nigrostriatal neurons of the patient, wherein the dopaminergic degeneration of nigrostriatal neurons is associated with a second diseased state or pathologic process, acquiring an image to detect the dopaminergic degeneration of nigrostriatal neurons in the striatal regions of the brain of the patient, detecting the presence or absence of the first diseased state or pathologic process, and detecting the presence or absence of the second diseased state or pathologic process. The radiopharmaceutical targeted to nigrostriatal neurons of some embodiments comprises ((2R,3R,11bR)-9-(3-[18F]fluoropropoxy)-3-isobutyl-10-methoxy-2,3,4,6,7,11b-hexahydro-1H pyrido[2,1a]isoquinolin-2-ol) ($^{18}$F-AV-133). In certain aspects of the invention, the effective amount of $^{18}$F-AV-133 includes from about 0.1 to about 20 mCi. In other aspects, the effective amount of $^{18}$F-AV-133 includes about 10 mCi.

In some embodiments, the step of administering the radiopharmaceutical targeted to β-amyloid plaque and the step of administering the radiopharmaceutical targeted to nigrostriatal neurons are performed concurrently. In other embodiments, the step of acquiring an image to detect the presence or absence of the β-amyloid plaque in the cortical regions of the brain of the patient and the step of acquiring an image to detect the dopaminergic degeneration of nigrostriatal neurons in the striatal regions of the brain of the patient are performed concurrently. In yet other embodiments, the steps of detecting the first diseased state or pathologic process and detecting the second diseased state or pathologic process are performed sequentially. In still other embodiments, the steps of detecting the first diseased state or pathologic process and detecting the second diseased state or pathologic process are performed concurrently.

Embodiments of the present invention are further directed to a method for detecting Alzheimer's Disease (AD) and Vascular Dementia (VaD) in a patient comprising administering an effective amount of a radiopharmaceutical targeted to β-amyloid plaque to a patient, wherein the β-amyloid plaque is associated with Alzheimer's Disease (AD), acquiring an image to detect the presence or absence of the β-amyloid plaque in the cortical regions of the brain of the patient, administering an effective amount of a perfusion imaging radiopharmaceutical, wherein the perfusion imaging radiopharmaceutical indicates blood flow in the brain of the patient and wherein a decrease in the perfusion imaging radiopharmaceutical signal is associated with Vascular Dementia (VaD), acquiring an image to detect perfusion of the brain of die patient, detecting the presence or absence of Alzheimer's Disease (AD) in the patient, and detecting the presence or absence of Vascular Dementia (VaD) in the patient. The perfusion imaging radiopharmaceutical of certain aspects of the present invention comprises $H_2{}^{15}O$. In other aspects, the perfusion imaging radiopharmaceutical comprises $^{13}NH_3$.

In certain embodiments, the step of administering the radiopharmaceutical targeted to β-amyloid plaque and the step of administering the perfusion imaging radiopharmaceutical are performed concurrently. In other embodiments, the step of acquiring an image to detect the presence or absence of the β-amyloid plaque in the cortical regions of the brain of the patient and the step of acquiring an image to detect perfusion of the brain of the patient are performed concurrently. In certain embodiments, the steps of detecting Alzheimer's Disease (AD) and detecting Vascular Dementia (VaD) are performed sequentially. In other embodiments, the steps of detecting Alzheimer's Disease (AD) and detecting Vascular Dementia (VaD) are performed concurrently.

DESCRIPTION OF THE DRAWINGS

For a fuller understanding of the nature and advantages of the present invention, reference should be made to the following detailed description taken in connection with the accompanying drawings, in which:

FIG. 1 is a simulated image of the brain of a healthy individual with no observable amyloid plaques and normal dopaminergic neurons;

FIG. 2 shows simulated activity curves for cortical regions of the brain of a healthy individual;

FIG. 3 shows simulated activity curves for striatal regions of the brain of a healthy individual;

FIG. 4 is a simulated image of the brain of an individual exhibiting the symptoms of Alzheimer's Disease;

FIG. 5 shows simulated activity curves for cortical regions of the brain of an individual exhibiting the symptoms of Alzheimer's Disease;

FIG. 6 shows simulated activity curves for striatal regions of the brain of an individual exhibiting the symptoms of Alzheimer's Disease;

FIG. 7 is a simulated image of the brain of an individual exhibiting the symptoms of Parkinson's Disease;

FIG. 8 shows simulated activity curves for cortical regions of the brain of an individual exhibiting the symptoms of Parkinson's Disease;

FIG. 9 shows simulated activity curves for striatal regions of the brain of an individual exhibiting the symptoms of Parkinson's Disease;

FIG. 10 is a simulated image of the brain of an individual with both Alzheimer's Disease and Parkinson's Disease;

FIG. 11 shows simulated activity curves for cortical regions of the brain of an individual with Alzheimer's Disease and Parkinson's Disease; and FIG. 12 shows simulated activity curves for striatal regions of the brain of an individual with Alzheimer's Disease and Parkinson's Disease.

DETAILED DESCRIPTION

Figure 1:
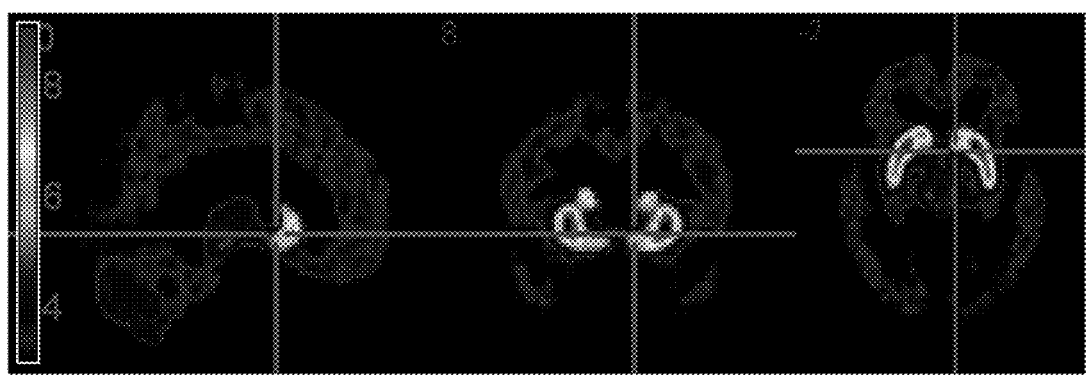
FIGS. 1-12 are simulated images of the brain created by the fusion of two separate image data sets in order to demonstrate the imaging of two or more targeted radiopharmaceuticals in the brain.

It is to be understood that this invention is not limited to the particular processes, compositions, or methodologies described, as these may vary. It is also to be understood that the terminology used in the description is for the purpose of describing the particular versions or embodiments only and is not intended to limit the scope of the present invention. Unless defined otherwise, all technical and scientific terms used herein have the same meanings as commonly understood by one of ordinary skill in the art. In case of conflict, the patent specification, including definitions, will prevail.

As used herein, the singular forms "a", "an" and "the" include plural reference, unless the context clearly dictates otherwise.

As used herein, the terms "Aβ-binding radiopharmaceutical" and "Aβ-aggregate binding radiopharmaceutical" refer to a compound, or pharmaceutically acceptable salt thereof that binds to amyloid-β peptide aggregates or amyloid plaques and that is radiolabeled with an isotope.

As used herein, the term "about" means plus or minus 10% of the numerical value of the number with which it is being used. Therefore, about 50% means in the range of 45%-55%.

"Administering", as used herein in conjunction with a diagnostic agent, such as, for example, a radiopharmaceutical, means to administer directly into or onto a target tissue or to administer the diagnostic agent systemically to a patient whereby the diagnostic agent is used to image the tissue or a pathology associated with the tissue to which it is targeted. "Administering" a composition may be accomplished by injection, infusion, or by either method in combination with other known techniques. Such combination techniques include, but are not limited to, heating, radiation and ultrasound.

As used herein, the term "healthy individual", "normal individual" or "normal healthy individual" refers to an individual who is not suspected to stiffer from any cognitive disorder such as, but not limited to, dementia or Alzheimer's Disease and/or an individual who is not suspected to have β-amyloid peptide aggregates in the cortex of the brain such as, but not limited to, someone who is less than 50 years of age.

The term "individual", as used herein, refers to a living creature.

An "isotopically-labeled", "radiolabeled", "labeled", "detectable" or "detectable amyloid binding" compound, "radioligand" or "radiolabeled pharmaceutical", as used herein, refers to a compound of the present invention where one or more atoms are replaced or substituted by an atom having an atomic mass or mass number different from the atomic mass or mass number typically found in nature (i.e., naturally occurring). Suitable radionuclides (i.e., "detectable isotopes") that may be incorporated in the compounds of the present invention include, but are not limited to, $^{11}$C, $^{13}$N, $^{15}$O, $^{18}$F, $^{75}$Br, $^{76}$Br, $^{77}$Br, $^{82}$Br, $^{99m}$Tc, $^{123}$I, $^{124}$I, $^{125}$I, and $^{131}$I. An isotopically labeled compound need only be enriched with a detectable isotope to a degree that permits detection with a technique suitable for the particular application.

"Optional" or "optionally", as used herein, may be taken to mean that a subsequently described structure, event or circumstance may or may not occur and that the description of the invention includes instances where the event occurs and instances where it does not.

The term "pathology" herein refers to an altered endogenous biological process that may be associated with the aberrant production of proteins, peptides, RNA and other substances associated with the disease process.

The term "patient" generally refers to any living organism to which the compounds described herein are administered and may include, but is not limited to, any non-human mammal, primate or human. Such "patients" may or may not be exhibiting the signs, symptoms or pathology of one or more particular diseased states.

A "therapeutically effective amount" or "effective amount" of a composition, as used herein, is a predetermined amount calculated to achieve the desired effect.

The term "tissue", as used herein, refers to any aggregation of similarly specialized cells united in the performance of a particular function.

Embodiments hereof provide a method for imaging structures in the brain of a patient relating to dementia or cognitive impairment, such as Alzheimer's Disease (AD), Parkinson's Disease (PD), Dementia with Lewy Bodies (DLB) and Vascular Dementia (VaD) using two or more different radiopharmaceuticals.

Various embodiments are directed to detection and discrimination between neurological disorders, and in particular embodiments, detection and discrimination between various neurological disorders that are each manifested in the symptoms of dementia. Certain aspects of the invention are directed to the detection and differential diagnosis of Alzheimer's Disease (AD), Parkinson's Disease (PD) and Dementia with Lewy Bodies (DLB).

In numerous embodiments of the present invention, a method of imaging is provided including a method of β-amyloid radiopharmaceutical imaging together with nigrostriatal neuronal imaging or metabolic imaging or perfusion imaging of the brain. In some embodiments, a first radiopharmaceutical such as, for example, a β-amyloid specific radiopharmaceutical, may be administered for imaging the presence of cortical pathology associated with AD and a second radiopharmaceutical such as, for example, a dopamine transporter (DAT) specific radiopharmaceutical or a vesicular monoamine transporter (VMAT) specific radiopharmaceutical for detecting PD or DLB, may be administered simultaneously or after a short period of time following administration of the first radiopharmaceutical for imaging the integrity of dopaminergic neurons in the striatal region of the brain. In another embodiment, a β-amyloid imaging radiopharmaceutical may be administered simultaneously with or within a short period of time, prior to or following, the administration of a cerebral perfusion imaging radiopharmaceutical. Such a combination of radiopharmaceuticals may allow the imaging of both amyloid plaque pathology (i.e. Alzheimer's Disease) and Vascular Dementia (VaD) in the same patient. PET and/or SPECT may be used to image the brain of the patient and detect the radiopharmaceuticals in embodiments of the present invention over a time period conducive to the pharmacokinetics of each radiopharmaceutical in the brain. In other embodiments, a combination of radiopharmaceuticals, such as, for example, $^{18}$F-AV-45 and $^{18}$FDG, provides for the imaging of both amyloid plaque pathology and brain metabolic activity in the same patient, thereby allowing for the assessment of the spatial correlation between plaque pathology and decreased metabolic utilization of glucose in the brain. Such methods may allow physicians to make a more accurate diagnosis of the presence or absence of AD, PD, DLB or VaD in a given subject in a shorter period of time than what is currently possible. Additionally, the methods of such embodiments may allow for the differential diagnosis of the underlying cause of, for example, memory impairment in patients with cognitive defects, or may allow for a better understanding of the relationship between certain brain pathologies and brain function in these neurodegenerative diseases.

Embodiments of the invention described herein provide a method that involves diagnostic imaging with two or more radiopharmaceuticals in the same dementia patient, where the radiopharmaceuticals target different underlying pathological, functional or perfusion processes in the brain, with at least one such radiopharmaceutical being an amyloid plaque imaging agent. This dual or multiple radiopharmaceutical imaging method for the brain will allow a physician or other medical professional to more accurately characterize a given dementia patient for the presence or absence of amyloid plaque (the most common cause of dementia), the presence or absence of dopaminergic degeneration caused by Lewy bodies (PD and DLB) and the presence or absence of cerebral perfusion defects (VaD). Various aspects of this method of imaging are directed to combining an amyloid plaque imaging radiopharmaceutical with at least one other imaging method (e.g. radiopharmaceutical) for evaluation of the underlying causes of dementia.

The method of various embodiments allows for the differential diagnosis of AD, PD, DLB and VaD and may be described in the following exemplary steps: administering a first radiopharmaceutical for detecting a first disease or target in the brain of a patient; administering a second radiopharmaceutical for detecting a second disease or target in the brain of the patient; waiting for a period of time adequate to allow uptake and binding of the administered radiopharmaceuticals in the appropriate regions of the brain of the patient; imaging one or more aspects of the brain of the patient; and reviewing the image(s) to make a diagnosis or other assessment (e.g. determine severity, prognosis, staging or response to treatment) of the patient. Depending on the radiopharmaceuticals used, the order of the foregoing steps may be varied. For example, in one embodiment, a single imaging session may provide a concurrent image of two or more radiopharmaceuticals in the brain. In other embodiments, imaging may be performed after both the first radiopharmaceutical injection as well as following the injection of the second radiopharmaceutical. The neurodegenerative disease processes may vary among embodiments and can be any individual disease or combination of diseases for which radiopharmaceutical imaging probes have been designed. For example, in particular embodiments, a first disease may be AD and a second (concurrent) disease may be PD, DLB or VaD. In certain embodiments of the present invention, methods are provided for imaging β-amyloid plaque (i.e. Alzheimer's disease) and a second neurodegenerative disease process, such as PD or DLB or VaD in the same subject in a single imaging session.

The first and second radiopharmaceuticals may be any radiopharmaceuticals known in the art that have been developed to detect different types of dementia. For example, methods of the invention may utilize any molecule with a high affinity for β-amyloid plaque together with a nigrostriatal imaging compound, such as a DAT or VMAT2 specific radiopharmaceutical. The radiopharmaceutical embodiments may also include any molecule with an affinity for a moiety associated with a central nervous system (CNS) disorder. Certain radiopharmaceutical embodiments may include a radiolabeled antibody, protein, peptide, nucleic acid, organic molecule, small molecule, polymer or a combination of these. However, it is to be noted that radiopharmaceuticals that are small molecules are generally preferred for this multiple radiopharmaceutical imaging procedure, due to their greater degree of diffusability in order to cross the blood-brain barrier, relative to proteins or polymeric materials.

Radiopharmaceuticals useful for the detection of β-amyloid, which could be used in this multiple radiopharmaceutical imaging methodology, include, but are not limited to, those described in WO 2006/014381, US 2003/0236391, US 2005/0043523, WO 2007/047204, WO 2007/086800, WO 2006/057323, EP 1815872, WO 2005/016888, EP 1655287, U.S. Pat. Nos. 6,696,039, 6,946,116, 7,250,525, WO 2006/078384, WO 2006/066104, WO 2007/126733, US 2006/269473, US 2006/269474, US2005/0271584, US 2007/0031328, Mathis et al., *J. Med. Chem.* 2003, 46: 2740-2754, Small et al., *N Engl. J. Med.* 2006, 355: 2652-2663, Zhang et al., *Nucl. Med. Biol.* 2005, 32: 799-809, Ono et al., *Nucl. Med. Biol.* 2002, 29:633-642, Ono et al., *Nucl. Med. Biol.* 2005, 32: 329-335, Qu et al., *Bioinorg. Med. Chem. Lett.* 2007, 17: 3581-3584, Kemppainen et al., *Neurology* 2007, 68: 1603-1606, Pike et al., *Brain* 2007, 130; 2837-2844, Klunk et al., *Ann. Neurol.* 2004; 55, 306-319, Verhoeff et al., *Am J. Geriatr. Psychiatry* 2004, 12, 584-595, and Newberg et al., *J. Nucl. Med.* 2006; 47, 748-754, each of which is hereby incorporated by reference in its entirety.

The nigrostriatal imaging radiopharmaceuticals useful in embodiments of the present invention for combination imaging with AD specific radiopharmaceuticals can be, for example, D2/D3 receptor imaging compounds or DAT or VMAT2 imaging radiopharmaceuticals. These types of radiopharmaceuticals have been described previously and are well known to one skilled in the art. Specific examples include, but are not limited to, [$^{123}$I-IBZM, $^{99m}$Tc]TRODAT-1, an iodinated cocaine derivative such as $^{123}$I-FP-CIT, $^{123}$I-β-CIT, and radiopharmaceutical derivatives of tetrabenazine such as $^{11}$C-dihydrotetrabenazine, and $^{18}$F-fluoropropyl dihydrotetrabenazine as described in Kung et al., *Semin. Nucl. Med.* 2003, 33(1), 2-13, Kung et al. *Nucl. Med. Biol.* 2007, 34, 239-246, and Kilbourn et al., *Nucl. Med. Biol.* 2007, 34, 233-237, each of which is hereby incorporated by reference in its entirety.

The radiopharmaceuticals of various embodiments of the present invention may be labeled with any radioisotopes that can be imaged with a PET or SPECT camera. For example, radiopharmaceuticals of various embodiments may be radiolabeled with radioisotopes such as, but not limited to, $^{76}$Br, $^{123}$I, $^{125}$I, $^{131}$I, $^{99m}$Tc, $^{11}$C, $^{18}$F, or other gamma- or positron-emitting radionuclides. In other embodiments, the radiopharmaceutical may be radiolabeled with a combination of radioisotopes.

The radioactive half-life of the radiopharmaceutical of embodiments of the present invention may vary depending on which radioisotope is utilized. Accordingly, in some embodiments, the radiopharmaceutical has a radioactive half-life of about 24 hours or less. In other embodiments, the radioactive half-life of the radiopharmaceutical may be about 12 hours or less, in still others, about 6 hours or less, and in some, about 2 hours to about 1 hour or less. In addition, the amount of radioactivity emitted by the radiopharmaceutical may vary among embodiments, and may depend upon various aspects of the procedure such as, for example, the period of time between administration and imaging or the physiology of the patient. For example, in some embodiments, 0.1 to 20 mCi (3.7 to 740 MBq) each of two different radiopharmaceuticals may be administered to an individual. Hence, an effective amount of each of the radiopharmaceutical may be from about 0.1 to about 20 mCi. In other embodiments, an effective amount of each radiopharmaceutical may be from about 0.1 to about 10 mCi. In still other embodiments, an effective amount of each radiopharmaceutical may be from about 0.1 to about 2 mCi. In further embodiments, lower effective amounts of radiolabeled compound may be possible. However, the precision of measurements and the quality of PET or SPECT images taken when a low dose of radiopharmaceutical is administered may deteriorate, and the time required for imaging the radiopharmaceutical may increase at lower injected doses.

In certain embodiments of the present invention, the first and second radiopharmaceuticals may be labeled with radioisotopes having different emission energies. For example, in one embodiment, a first radiopharmaceutical may be labeled with $^{18}$F and a second radiopharmaceutical may be labeled with $^{123}$I. The gamma energies of $^{18}$F and $^{123}$I (511 KeV and 159 KeV, respectively) may be separated at least in part with SPECT cameras using energy discrimination techniques well known to those in the art such as, for example, those described in Sandler et al., *J. Am. Coll. Cardiol.*, 1995, 26: 870-878 and U.S. Pat. No. 3,904,530, both of which are hereby incorporated by reference in their entireties.

In some embodiments, the first and second radiopharmaceuticals may be administered individually in, for example, separate injections. In other embodiments, the first and second radiopharmaceuticals may be administered concurrently in, for example, a single injection. When administered individually, administration of the second radiopharmaceutical may occur following administration of a first radiopharmaceutical after an appropriate period of time of from seconds to several hours. For example, in some embodiments, the second radiopharmaceutical may be administered about 15 seconds to about 2 hours following administration of the first radiopharmaceutical. In certain embodiments, following separate administrations, the radiopharmaceuticals may be imaged sequentially or concurrently, as long as the total procedure time is of reasonable duration for the patient. In some embodiments, the dual radiopharmaceutical imaging method may be completed within less than approximately 4 hours and preferentially within 2 hours or less. In various embodiments, the second radiopharmaceutical may be administered about 30 seconds to about 1 hour or about 1 minute to about 30 minutes or about 5 to about 15 minutes following administration of the first radiopharmaceutical.

The radiopharmaceuticals of embodiments of the present invention may be administered by any procedure known in the art including, but not limited to, parenterally by, for example, intravenous injection, intramuscular injection or subcutaneous injection, intraperitoneally, or via buccal or nasal spray. In certain embodiments, the radiopharmaceuticals may be administered by bolus injection or infusion. The first and second radiopharmaceuticals may be individually administered systemically or locally. For example, in some embodiments, the first and/or second radiopharmaceutical may be administered systemically by, for example, intravenous injection, and in other embodiments, the first and/or second radiopharmaceuticals may be administered directly by, for example, injection into the brain or the carotid artery. In some embodiments, the first and second radiopharmaceuticals may be administered by the same procedure, and in other embodiments, the radiopharmaceuticals may be administered by different administration procedures. For example, in one embodiment, a first radiopharmaceutical may be administered systemically by intravenous bolus injection, and the second radiopharmaceutical may be administered by local bolus injection directly into the carotid artery of the patient.

In some embodiments of the multiple radiopharmaceutical imaging method, the steps of administering the first and second radiopharmaceuticals may be followed by a step of waiting for a period of time. The waiting period may vary among embodiments of the invention and is generally a period sufficient for the radiopharmaceuticals being utilized. For example, the waiting period may be a time period sufficient for at least a portion of a systemically administered radiopharmaceutical to be deposited into the target tissue, such as, for example, the brain, and bind to the substrate of the radiopharmaceutical composition, such as, for example, Aβ plaque, DAT or VMAT2. Additionally, the waiting period may vary among embodiments as a result of, for example, manner, location, and amount of radiopharmaceutical administered, affinity of the radiopharmaceutical for target tissue, and the health of the individual. Embodiments of the invention are not limited by the waiting time, which may generally be from, for example, about 15 minutes to about 4 hours. In other embodiments, the waiting period may be from about 15 minutes to about 3 hours or about 30 minutes and about 2 hours or about 30 minutes and about 1.5 hours or about 45 minutes and about 1 hour. In additional embodiments of the present invention, a waiting step follows the administration of a first radiopharmaceutical followed by acquiring a PET or SPECT scan, administering a second radiopharmaceutical, waiting a period of time and then acquiring a PET or SPECT scan.

The step of imaging may be carried out by any procedure known in the art that may allow the imaging of the radiopharmaceuticals administered. For example, in some embodiments, imaging may be carried out by PET or SPECT imaging. In other embodiments, the imaging may be carried out by both PET and SPECT or by combined imaging methods such as PET/CT (PET with concurrent computed tomography imaging) or PET/MRI (PET with concurrent magnetic resonance imaging). The imaging procedure may result in one or more images of the region of observation of the patient, and in embodiments in which imaging results in more than one image, these multiple images may be combined, overlaid, added, subtracted, color coded or otherwise fused and mathematically manipulated by any method known in the art. The first and second radiopharmaceuticals may be imaged individually or concurrently. In some embodiments in which the radiopharmaceuticals are imaged individually, the order in which the radiopharmaceutical imaging procedure is performed is not crucial and may depend on the half-life of the radioisotope, the dose of the radiopharmaceutical administered as well as the pharmacokinetics of each radiopharmaceutical in the region of observation. In certain embodiments, each imaging procedure may be performed within the same 24 hour period and in particular embodiments, within a 1-4 hour time period or within less than a 2 hour time period. The image produced may be a digital or analog image that may be displayed as a "hard" image on, for example, printer paper, photographic paper or film, or as an image on a screen, such as for example, a video or LCD screen.

The images produced using the imaging procedure embodied in the present invention may be analyzed by any method known in the art. For example, in one embodiment, the image may be analyzed by a physician or another medical professional who visually observes the derived images and grades the disease state based on the observable presence of the first and/or second radiopharmaceutical in the images produced. In another embodiment, the images may be analyzed by a processor or processor system. For example, in one embodiment, image data derived from a PET or SPECT scan can be inputted into a processor that identifies individual pixels or groups of pixels whose brightness is greater than a predetermined threshold or an average background, and identified pixels may be characterized as indicating the presence of a radiopharmaceutical. In another embodiment, the image data may be derived from images scanned and inputted into a processor. In such embodiments, a similar process that identifies bright spots on the image may be used to locate the radiopharmaceuticals in the image. In certain embodiments, the analysis of the image may further include determining the intensity, concentration, strength or combination thereof of the output brightness, which may be correlated to the amount of radiopharmaceutical in the image, an area or region of the image, or a particular spot on the image. Without wishing to be bound by theory, an area or spot on an image having a greater intensity than other areas or spots may hold a higher concentration of radiopharmaceutical targeted to, for example, β-amyloid, DAT or VMAT and, thus, may have a higher concentration of the radioisotope attached to the region where the radiopharmaceutical localizes in the brain. Images may also be analyzed by the spatial location of regions of interest to which the administered radiopharmaceuticals are targeted. In other embodiments, analysis of the pharmacokinetics of the administered radiopharmaceuticals may provide information on the appropriate timing of injection of each radiopharmaceutical, which is yet another way to differentiate between the two administered radiopharmaceuticals in the acquired images.

By identifying areas, regions or spots on an image that correlate to the presence of a radiopharmaceutical, the presence or absence of a diseased state may be determined. For example, in embodiments in which a first radiopharmaceutical for detecting β-amyloid is used and a second radiopharmaceutical for detecting DAT or VMAT is used, each image may be used to diagnose the presence or absence of AD, PD and DLB individually in each image. In other embodiments, the images may be used to diagnose AD and/or PD and/or DLB individually from two or more images taken at different time points, and in still other embodiments, the images may be used to concurrently diagnose AD, PD and DLB in each of two or more images taken at different time points.

In particular embodiments, a radiopharmaceutical for detecting AD by imaging β-amyloid or a metabolic tracer (e.g., $^{18}$F-FDG) may be administered first to a patient and images of the patient may be acquired followed by administration of a nigrostriatal imaging compound and imaging of the patient for detecting PD and DLB. In other embodiments, the same radiopharmaceuticals may be administered and the patient may be imaged in reverse order to provide similar diagnostic information.

Alternatively, in still other embodiments, both radiopharmaceuticals may be administered to the patient within minutes of each other followed by PET or SPECT imaging for both compounds simultaneously. In such embodiments, radiopharmaceuticals and diseased states may be selected for the detection of structures in separate regions of the brain of a patient. For example, the AD diagnostic radiopharmaceutical binds primarily to β-amyloid in the cortical region of the brain, which is spatially separated from the DAT or VMAT2 radiopharmaceutical, which binds to dopaminergic neurons in the striatum of the brain. Therefore, a single image acquired of a patient who has been administered both β-amyloid and DAT or VMAT2 detecting radiopharmaceuticals may be analyzed separately for AD and PD and/or DLB concurrently because the spatial separation of the two radiopharmaceutical signals in the brain allows the physician to observe both signals. The amount of spatial separation may vary among embodiments, and may depend on factors, such as, for example, the distribution of disease associated structures, the sensitivity and spatial resolution of the imaging device, the radiopharmaceuticals used and the skill of the practitioner, among other factors. In some embodiments, spatial separation between disease-associated structures may be at least about 5 mm apart, at least about 10 mm apart, or at least about 50 mm apart. In other embodiments, the spatial separation may be smaller. In yet further embodiments, physical attributes associated with the disease-associated structures such as, for example, concentration of disease-associated structures and size of the structures or the characteristics of the radiopharmaceutical utilized such as, for example, the type of radioisotope associated with the radiopharmaceutical or ability to spectrally separate different radioisotopes may provide evidence of one disease-associated structure versus another. For example, spatially overlapping structures may be separately imaged if the energies of the radioisotopes attached to the radiopharmaceuticals are resolvable by energy discrimination methods available on many SPECT cameras. In some embodiments, PET radiopharmaceuticals labeled with different radioisotopes may be separated in a PET brain image based on different rates of decay for the radioisotopes employed (e.g. by imaging the short-lived radioisotope prior to imaging the longer-lived radioisotope).

The imaging methods described in embodiments of the invention may provide a larger amount of diagnostic information in a relatively shorter period of time, compared to images separately created on a different imaging day for each radiopharmaceutical utilized. As such, using embodiments of methods of the invention, a physician or other medical professional may determine the presence or absence of, for example, β-amyloid plaque, decreases in DAT or VMAT transporters, and/or decreases in cerebral perfusion more quickly thereby diagnosing or monitoring AD, PD and/or DLB and/or VaD more quickly than currently possible by imaging individual radiopharmaceuticals over several imaging sessions.

EXAMPLES

In order that the invention disclosed herein may be more efficiently understood, the following example is provided. The following example is for illustrative purposes only and is not to be construed as limiting the invention in any manner.

Example 1

Dual Radiopharmaceutical Imaging of β-Amyloid and Nigrostriatal Neurons

Data was generated from the radiopharmaceutical imaging of β-amyloid plaque and nigrostriatal dopaminergic degeneration utilizing dual radiopharmaceuticals. The radiopharmaceuticals utilized included $^{18}$F-AV-45, which targets β-amyloid plaque and $^{18}$F-AV-133, which targets nigrostriatal neurons. The radiopharmaceuticals were administered via intravenous injection to subjects who were clinically diagnosed with Parkinson's Disease (PD) or Alzheimer's Disease (AD).

Data was analyzed for PD patients (PD_AV133) and Healthy Controls (HC_AV133) as well as for AD patients (AD_AV45) and Healthy Controls (HC_AV45). Data and images derived from subjects in each category were analyzed individually. Data and images from an average of 4 subjects in each respective category was also analyzed and used as the basis of this protocol. The optimal imaging protocol was judged based on the following criteria: clarity of images/data in the cortical, grey, and white volumes of interest (VOIs) of the brain (relating to diagnosis of AD) and the striatal VOIs of the brain (relating to diagnosis of PD/DLB); ease and level of certainty of the individual diagnoses of the presence or absence of AD, PD, and DLB; minimum level of radiation injected into a patient; and minimum protocol completion time.

Figure 4:
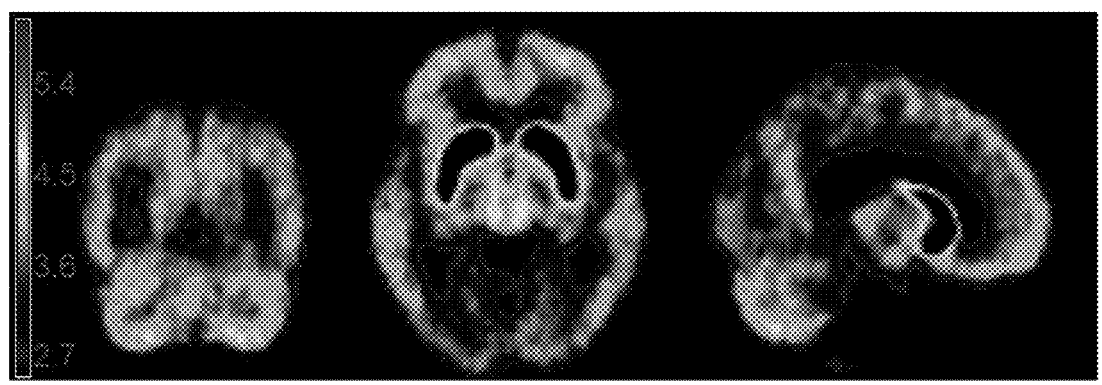
Figure 7:
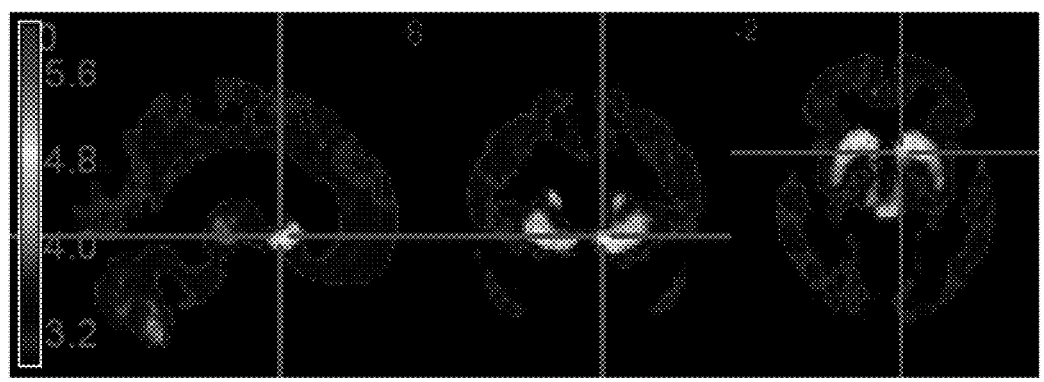
Figure 10:
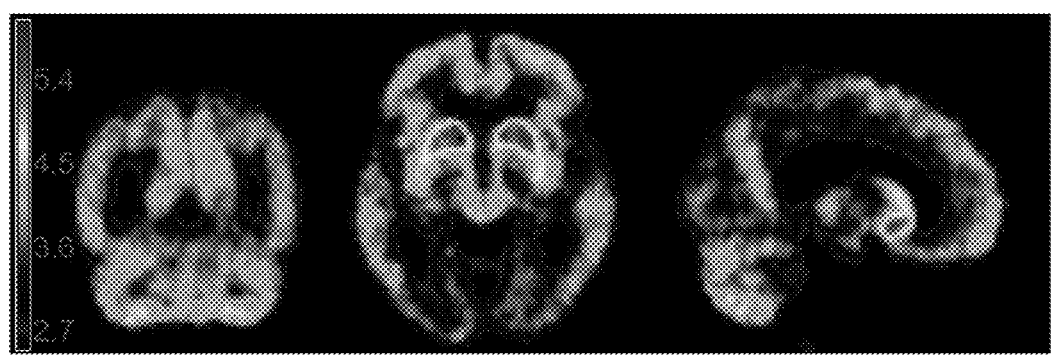

Simulated (i.e. fused) images of the brains of a healthy individual, an individual exhibiting symptoms of AD, an individual exhibiting symptoms of PD, and an individual exhibiting symptoms of both AD and PD are illustrated in FIGS. 1, 4, 7 and 10, respectively. FIGS. 1, 4, 7 and 10 were created by the fusion of two separate image data sets, one from a PET scan of an $^{18}$F amyloid plaque-binding radiopharmaceutical ($^{18}$F-AV-45) and one from a PET scan of an $^{18}$F VMAT2 targeted radiopharmaceutical ($^{18}$F-AV-133). FIG. 1 is a simulated image of the brain of a healthy individual with no observable amyloid plaques and normal dopaminergic neurons (imaged between 70 and 80 minutes). As can be seen, the fused image shows no appreciable cortical brain signal from $^{18}$F-AV-45, which is indicative of the lack of amyloid plaque deposits. In addition, FIG. 1 shows a strong signal in the nigrostriatal region from the VMAT2 imaging compound $^{18}$F-AV-133, which is typical for someone without signs or symptoms of PD or DLB. FIG. 4 shows a simulated image of the brain of an individual with clinical signs of AD. Amyloid plaque deposits are visible in the frontal region of the brain (orange) (imaged between 70 and 80 minutes) from the $^{18}$F-AV-45 radiopharmaceutical signal. This figure also shows a normal uptake of the $^{18}$F-AV-133 radiopharmaceutical in the nigrostriatal region of the brain. This image pattern is consistent with a pure AD diagnosis, with no evidence of loss of striatal neurons (which would be observed if PD or DLB were also present). FIG. 7 is a simulated image of the brain of an individual exhibiting the symptoms of PD. As shown in FIG. 7, lack of intensity in the striatal regions of the $^{18}$F-AV-133 radiopharmaceutical is indicative of dopaminergic degeneration and is visible (imaged between 70 and 80 minutes). In addition, this image does not show evidence of amyloid signal in the cortical brain regions from $^{18}$F-AV-45. This image pattern is consistent with a pure PD diagnosis, without evidence of AD amyloid plaque pathology. FIG. 10 shows a simulated fused image of the brain of an individual with both AD and PD. Amyloid plaques (green) (from $^{18}$F-AV-45 retention in cortical brain) and lack of intensity in the striatal regions (due to diminished uptake of AV-133 from losses of strial neurons in PD) are both visible (imaged between 70 and 80 minutes).

The Statistical Parametric Mapping (SPM2) application in MATLAB® (Version 7.3 R2006b, MathWorks, Inc.) was used to align the raw images and create a mean image from the image set. The mean image was normalized to a SPECT template, although in other experiments, other templates were used. Using the image viewer application in MRICro, the normalized mean image was compared with the template image to confirm that the two images align. Using SPM2, the realigned images from an image set were normalized to the normalized mean image for that set. In MATLAB®, volume of interest (VOI) images were overlaid on the normalized images, and the radioactive counts per voxel per minute for specific brain regions were extracted into a Microsoft Office Excel spreadsheet. (voxel size was 8 mm$^3$). Specific brain regions included left and right caudate, left and right anterior putamen, left and right posterior putamen, precuneus, posterior cingulate, cerebellum (grey), frontal lobe, occipital lobe, parietal lobe and temporal lobe. Standardized uptake values (SUVs) were calculated from the counts extracted from the images. The dose administered to each subject was then normalized to 10, and the resulting number was multiplied with the counts for each brain region. New SUVs were in turn recalculated from the new values. The SUVs from four subjects in each category were averaged together, and four separate disease state possibilities were identified: (1) AD_AV45 & HC_AV133, (2) PD_AV133 & HC_AV45, (3) AD_AV45 & PD_AV133, and (4) HC_AV45 & HC_AV133.

Figure 2:
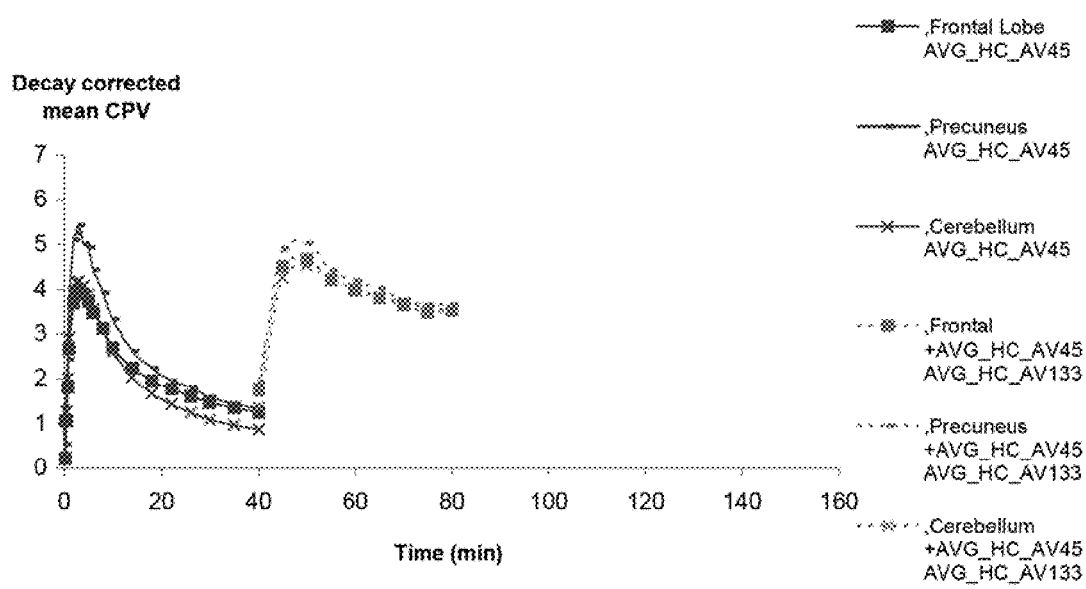
Figure 3:
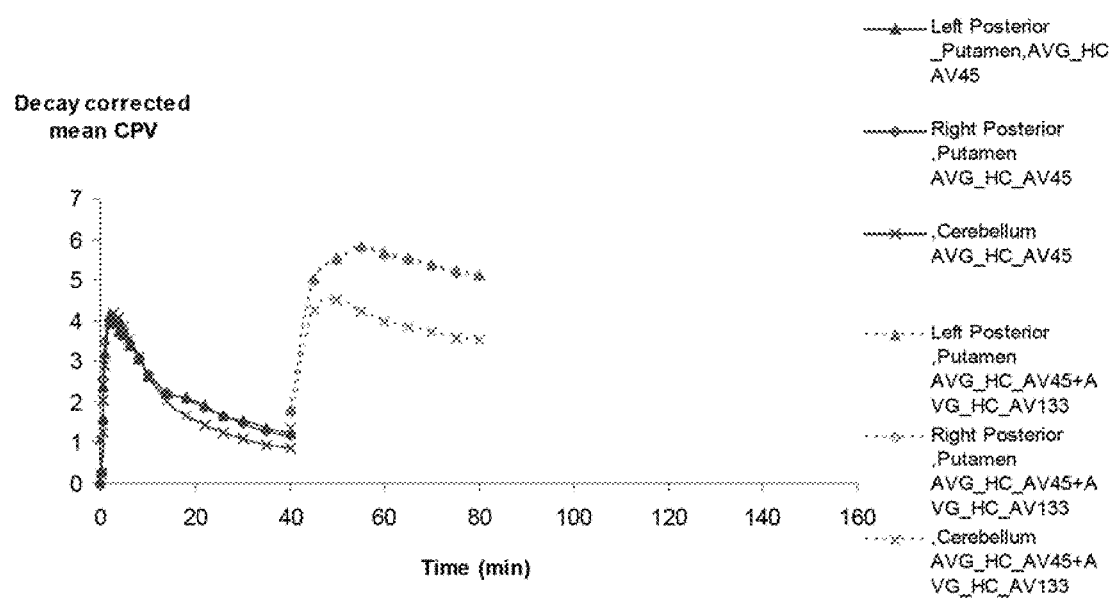
Figure 5:
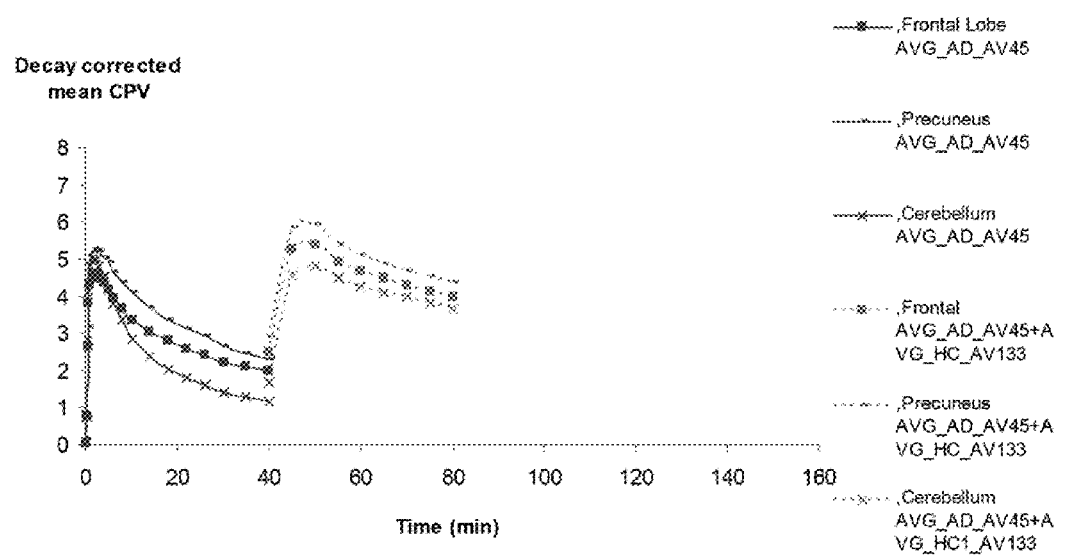
Figure 6:
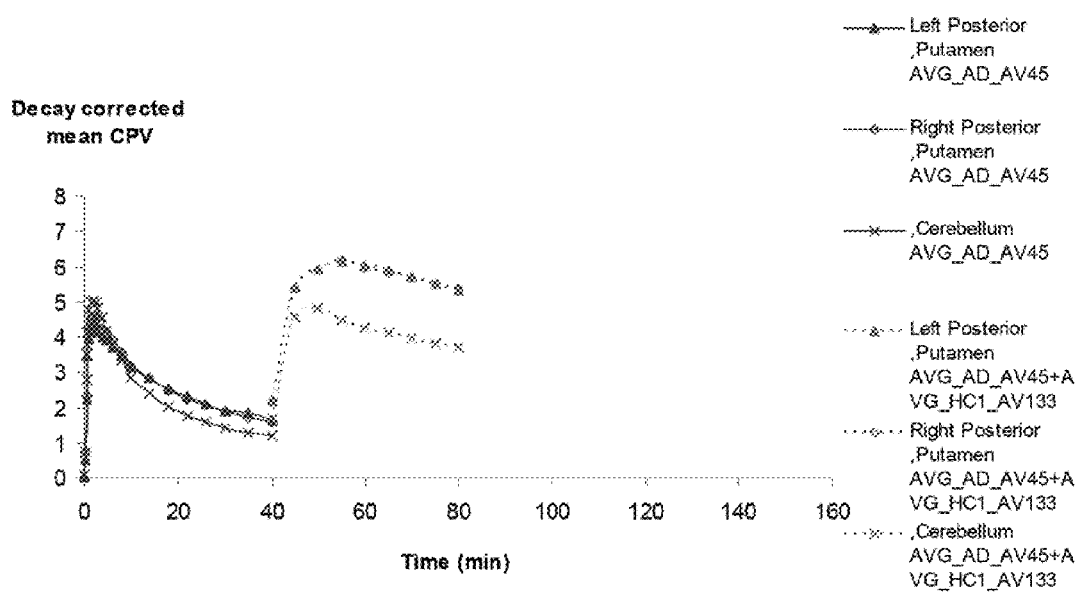
Figure 8:
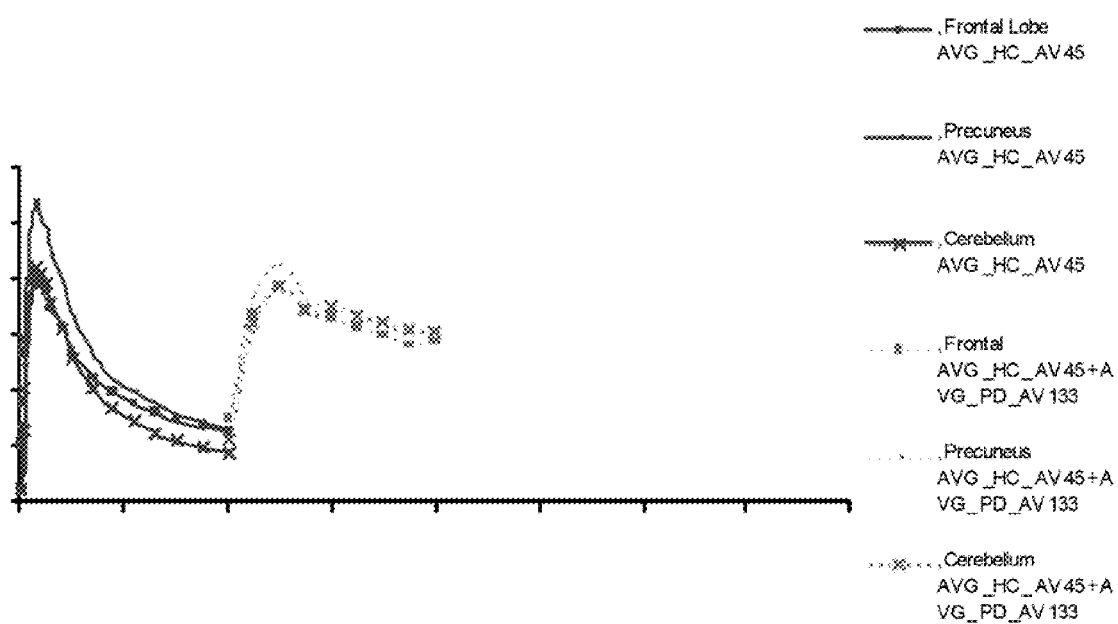
Figure 9:
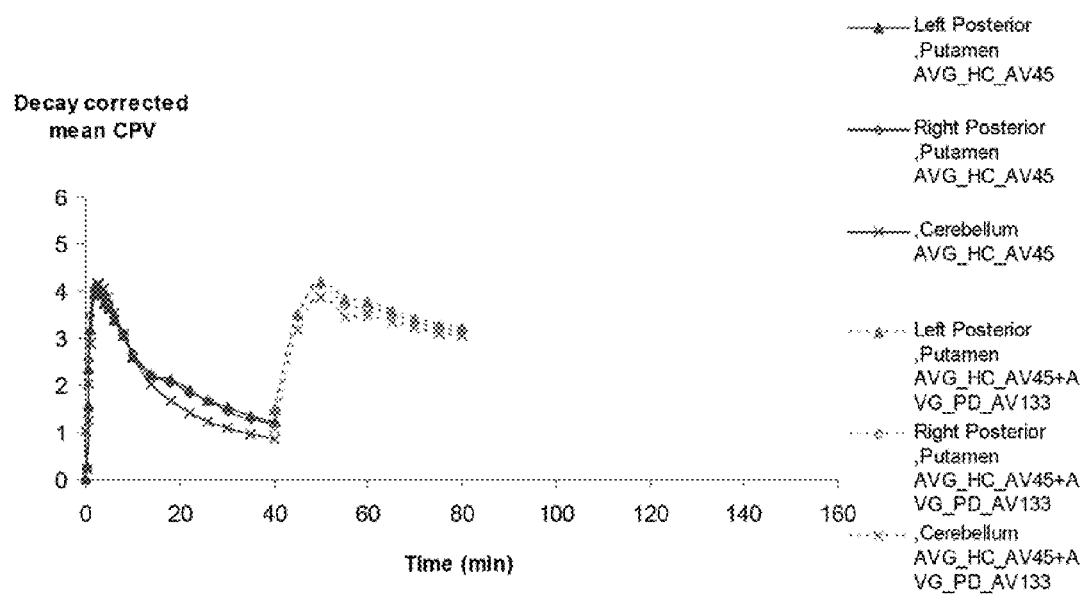
Figure 11:
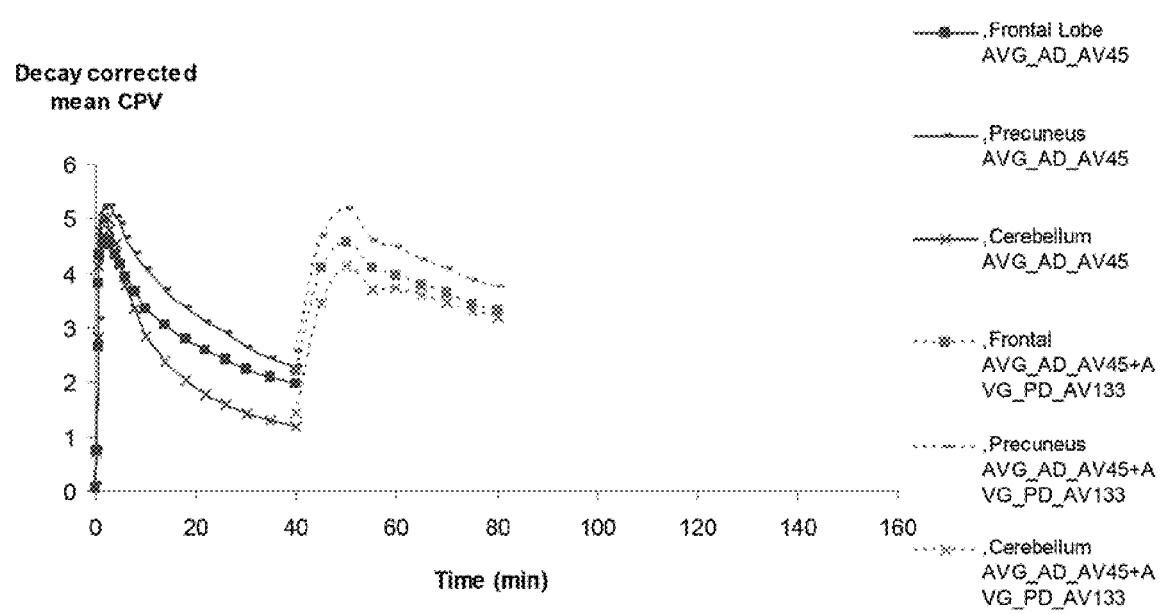
Figure 12:
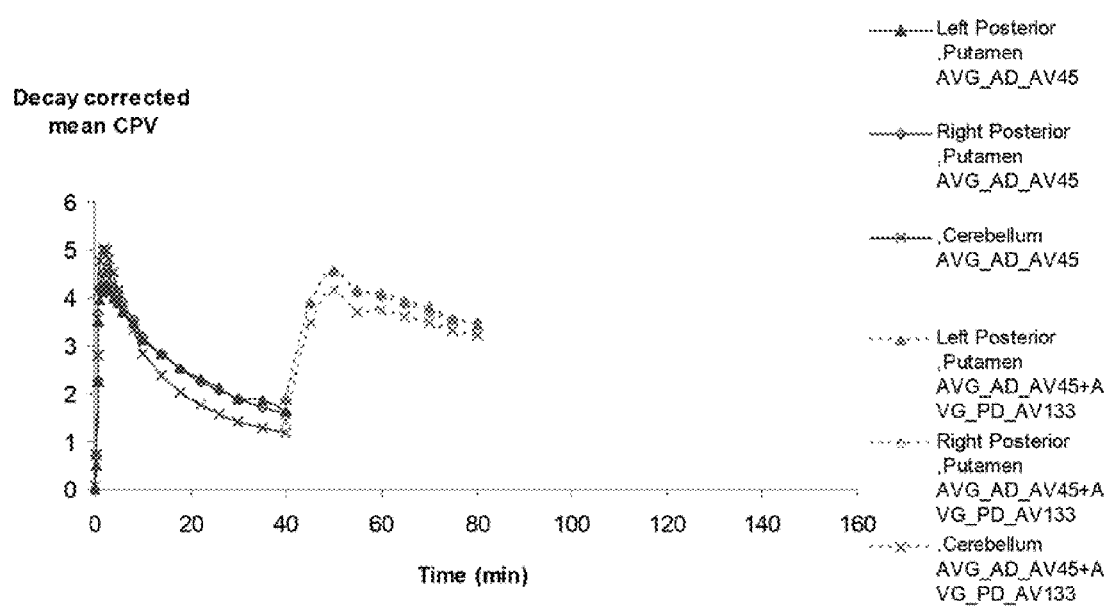

For each case shown in FIGS. 1, 4, 7 and 10, the SUVs from the frontal, precuneus and cerebellum regions (cortical regions) for the subjects were plotted simultaneously with time and separate plots were created for the SUVs from the striatal regions (i.e., left and right posterior putamen and cerebellum) of the subjects simultaneously with time, as illustrated in FIGS. 2, 3, 5, 6, 8, 9, 11 and 12. The cortical regions are where amyloid plaques are found in the brain using the $^{18}$F-AV-45 radiopharmaceutical, while the striatal regions contain dopaminergic neurons detected with the $^{18}$F-AV-133 radiopharmaceutical. In particular, FIG. 2 shows simulated activity curves for cortical regions of the brain of a healthy individual and FIG. 3 shows simulated activity curves for striatal regions of the brain of the healthy individual. FIGS. 5 and 6 show simulated activity curves for cortical and striatal regions of the brain, respectively, for an individual with AD. FIGS. 8 and 9 show simulated activity curves for cortical and striatal regions of the brain, respectively, of an individual with PD while FIGS. 11 and 12 show simulated activity curves for cortical and striatal regions of the brain, respectively, of an individual with AD and PD. These plots demonstrated the pharmacokinetics of each administered radiopharmaceutical, and such information was utilized in considering dissimilar injection times, and dose normalization. Whenever the two radiopharmaceuticals were considered as being simultaneously present in the brain, the SUVs from both radiopharmaceuticals for each region were summed together, and the summed SUVs were plotted. This allowed for the simulation/prediction of the interaction and possible interference of activity of one radiopharmaceutical with the other when both are present in the brain during the imaging of the subject.

Images from these subjects were further analyzed. The calculations performed on the radioactive counts (i.e., dose normalization, summation of activity) were also performed on the images, producing a prospective image for the visual inspection by physicians or other medical professionals.

Through analyzing and experimenting with the plots and images described above, a protocol for the simultaneous imaging of AD plaques and dopaminergic neuronal degeneration was created. This protocol included the following: administering 10 mCi of $^{18}$F-AV-45 to a subject; waiting a period of 30 minutes; 10 minute imaging acquisition period to detect the presence or absence of amyloid plaques in the cortical regions of the brain; then administering 10 mCi of $^{18}$F-AV-133 to the same subject (about 50 minutes after the start of protocol); waiting a period of 30 minutes; 10 minute imaging acquisition period to detect the presence or absence of dopaminergic neuronal degeneration in the striatal regions of the brain ($^{18}$F-AV-45 washout and radioactive decay is essentially complete at this point, thus minimally interfering with $^{18}$F-AV-133 activity). The total protocol time was about 80 to 90 minutes. When analyzing the images gleaned from the two imaging acquisition periods, the image intensity was visually normalized to the cerebellum to enable a clear and easy diagnosis of the presence or absence of AD, PD or DLB.

Various modifications of the invention, in addition to those described herein, will be apparent to those skilled in the art from the foregoing description. Such modifications are intended to fall within the scope of the appended claims.

What is claimed is:

1. A method for detecting or ruling out multiple neurodegenerative diseased states or pathologic processes in a patient comprising:
    administering an effective amount of $^{18}$F-AV-45 to a patient, wherein β-amyloid is associated with a first diseased state or pathologic process;
    acquiring an image to detect the presence or absence of β-amyloid plaque in the cortical regions of the brain of the patient;
    administering an effective amount of $^{18}$F-AV-133, wherein dopaminergic degeneration of nigrostriatal neurons is associated with a second diseased state or pathologic process;
    acquiring an image to detect dopaminergic degeneration of nigrostriatal neurons in the striatal regions of the brain of the patient;
    detecting the presence or absence of the first diseased state or pathologic process; and
    detecting the presence or absence of the second diseased state or pathologic process.

2. The method of claim 1, wherein the effective amount of $^{18}$F-AV-45 comprises from about 0.1 to about 20 mCi.

3. The method of claim 1, wherein the effective amount of $^{18}$F-AV-45 comprises about 10 mCi.

4. The method of claim 1, wherein the effective amount of $^{18}$F-AV-133 comprises from about 0.1 to about 20 mCi.

5. The method of claim 1, wherein the effective amount of $^{18}$F-AV-133 comprises about 10 mCi.

6. The method of claim 1, wherein the first diseased state is at least one of dementia, cognitive impairment, Alzheimer's Disease (AD), Parkinson's Disease (PD), Dementia with Lewy Bodies (DLB), Vascular Dementia (VaD), and combinations thereof.

7. The method of claim 1, wherein the second diseased state is at least one of dementia, cognitive impairment, Alzheimer's Disease (AD), Parkinson's Disease (PD), Dementia with Lewy Bodies (DLB), Vascular Dementia (VaD), and combinations thereof.

8. The method of claim 1, wherein the step of administering the radiopharmaceutical targeted to β-amyloid plaque and the step of administering the radiopharmaceutical targeted to nigrostriatal neurons are performed concurrently.

9. The method of claim 1, wherein the step of acquiring an image to detect the presence or absence of the β-amyloid plaque in the cortical regions of the brain of the patient and the step of acquiring an image to detect the dopaminergic degeneration of nigrostriatal neurons in the striatal regions of the brain of the patient are performed concurrently.

10. The method of claim 1, wherein the steps of acquiring images comprise positron emission tomography (PET) imaging, single photon emission computed tomography (SPECT) imaging, PET with concurrent computed tomography imaging (PET/CT), PET with concurrent magnetic resonance imaging (PET/MRI), SPECT with concurrent CT imaging (SPECT/CT), or a combination thereof.

11. The method of claim 1, further comprising the step of normalizing the image intensity of the acquired images to the cerebellum of the brain of the patient.

12. The method of claim 1, wherein the steps of detecting the first diseased state or pathologic process and detecting the second diseased state or pathologic process are performed concurrently.

* * * * *